United States Patent [19]

Solazzi

[11] Patent Number: 4,665,759

[45] Date of Patent: May 19, 1987

[54] SAMPLE CUP WITH A CANTILEVER BEAM VENTING MEANS

[75] Inventor: Monte J. Solazzi, Eastchester, N.Y.

[73] Assignee: Chemplex Industries, Inc., Eastchester, N.Y.

[21] Appl. No.: 778,080

[22] Filed: Sep. 20, 1985

[51] Int. Cl.⁴ .................. G01N 37/00; H05G 1/00
[52] U.S. Cl. .................. 73/864.91; 356/246; 378/208
[58] Field of Search ............ 73/864.91; 356/246; 422/102; 378/204, 47, 79; 206/628; 250/428; D24/2, 29; 220/268, 269, 368, 369, DIG. 27

[56] References Cited

U.S. PATENT DOCUMENTS

| | | | |
|---|---|---|---|
| 238,693 | 2/1976 | Solazzi | D24/2 |
| 2,864,279 | 12/1958 | Phifer | 250/428 |
| 3,378,684 | 4/1968 | Mentink et al. | 250/428 |
| 4,346,299 | 8/1982 | Mitteldorf et al. | 206/527 |
| 4,409,854 | 10/1983 | Solazzi | 356/246 |
| 4,448,311 | 5/1984 | Houser | 356/246 |

Primary Examiner—Stewart J. Levy
Assistant Examiner—Robert R. Raevis
Attorney, Agent, or Firm—Arthur L. Plevy

[57] ABSTRACT

A sample cup for use in holding a sample for spectrochemical analysis consists of a main cell member which is cup-shaped and has a closed top surface. Located on the top surface is a venting means which includes a beam-like section of a given thickness extending along the top surface near the center. The beam is surrounded by a thinner area integrally fabricated with the top surface. Extending upwardly from the surface of the beam is a post which when pushed downwardly crosses the cantilever beam to rupture the thin area thus creating a venting path for pressure equalization. The cantilever beam automatically returns due to spring action to its original position thus preventing excessive material from escaping from the hollow confines of the sample cup.

8 Claims, 2 Drawing Figures

SAMPLE CUP WITH A CANTILEVER BEAM VENTING MEANS

BACKGROUND OF THE INVENTION

This invention relates to a sample cup for use in holding specimens for spectrochemical analysis and more particularly to such a cup including means for venting the same.

Sample cups for spectrochemical analysis are used in the prior art to hold or contain liquids, solids and powdered specimens under normal atmospheric pressure, gas pressure or in vacuum for analysis such as energy and wavelength dispersion and optical emission methods. These cups are in wide spread use and have been the subject matter of many patents.

A basic sample cup consists of three components as a cup-shaped cell body having closed bottom and an opened top, an annular collar and a snap-on ring. The collar and the snap-on ring serve to secure a sheet of plastic material such as MYLAR, a trademark for a polyester sheet material of E. I. duPont de Nemours and Company, to cover the open top of the cell when the hollow of the cell is filled with a specimen to be analyzed. Such cells are available from many sources such as Chemplex Industries, Inc., 140 Marbledale Road, Eastchester, N.Y. 10707, the assignee herein.

The cells of the priar art typically have venting means which may comprise a smaller area on the closed bottom surface of the cell which can be punctured or pierced by means of a sharp point such as a needle, a ballpoint pen or some other device. The pierced hole serves as a vent which is used to equalize pressure which is in the sample cup.

An example of a typical venting means is shown in U.S. Pat. No. 4,409,854 entitled Sample Cup with Venting Means for Use in X-ray Spectroscopy, issued on Oct. 18, 1983 to Michael C. Solazzi and assigned to the assignee herein.

During the spectrochemical analytic investigation of specimens characterized with high abrogation properties in air, the entire assembed sample cup with the plastic sheet covering the cup is emplaced within a vacuum or an inert gas environment.

Under conditions where pressure equalization is not implemented, the plastic sheet will distend or bow outwardly due to the vacuum or lower pressure. This then places the surface of the sheet closer to the excitation source which may be an x-ray tube or other device. The surface of the sheet of plastic is commonly defined as the sample plane. Thus a variation in the distance from the sample plane to the source of excitation operates to alter the intensity of the characteristic radiation of the specimen and also the intensity of radiation impinging upon the sample from the excitation source.

The variations result in erroneous quantatative data and hence cannot be tolerated. As indicated, for applications in a vacuum environment, the thin plastic film distends or bows out (convex) which decreases the distance from the sample to the excitation soruce. For applications in a gaseous environment (positive pressure) the thin plastic film distends or is drawn into the hollow of the cell providing a concave surface. This effect increases the distance between the sample plane and the excitation source resulting in lower values of analytical data.

In order to equalize the pressure, the prior art had a section in the closed bottom surface of the cell which allowed one to pierce a hole in the cup or vent the cup. This technique relied upon the skill of the operator, and if too much force were employed, the hole would be too large and a sample might become contaminated or parts of the cup dislodged.

In other prior art techniques such as the techniques referred to in the above noted patent, the venting means were relatively complicated resulting in difficulty and in increased cost in molding and providing such structures. Other techniques such as that shown in U.S. Pat. No. 4,346,299 entitled Cell for Containing Fluid to be Analyzed by X-ray Spectroscopy, issued on August 1982 to A. J. Mittledorf et al show venting means which are disposed off center and which include a vertical pin or post which is also off center on a generally circular structure which defines the puncturing means.

In this patent the puncturing means includes a semicircular portion of minimal thickness which provides an area of weakness and another semi-circular portion of a greater thickness. Located between the two areas in an upstanding post which when pivoted in the direction of the thick wall causes the thin wall to rupture and hence provide a venting means. This technique is particularly difficult to utilize as it requires a pivoting motion of the pin, and hence the operator may drop the cup or the pivoting motion may cause an excessive material loss while providing possible sample contamination.

It is, therefore, an object of the present invention to provide a sample cup including improved venting means which enable an operator to provide venting of the cup in a rapid and precise manner.

BRIEF DESCRIPTION OF THE PREFERRED EMBODIMENT

In a sample cup body for retaining a specimen to be subjected to spectrochemical analysis said cup body having a closed bottom surface and an open top, venting means located on said closed bottom surface and comprising an extended cantilever beam section positioned on said bottom surface and surrounded by a thin integrally formed section, said thin section being thinner than said bottom surface with an extending post positioned on said cantilever beam section and adopted when pushed downwardly to cause a rupture of said thin section to thereby provide said venting means.

DETAILED DESCRIPTION OF THE FIGURES

Figure 1:
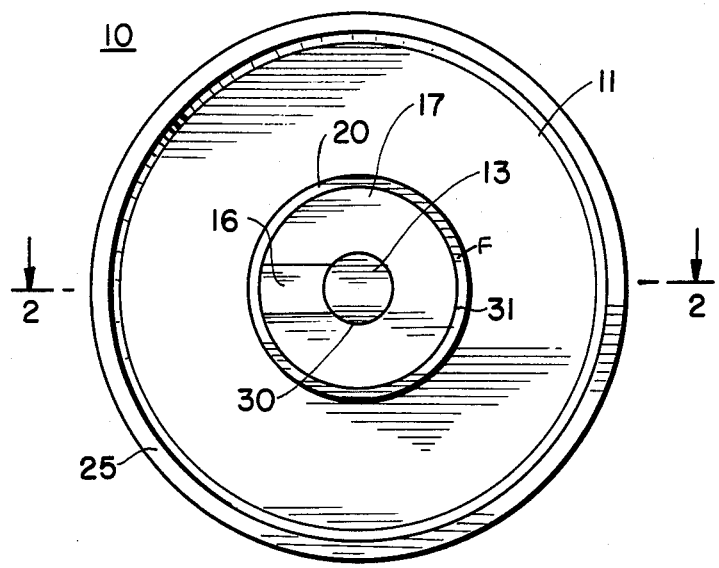
FIG. 1 is a top plane view of a sample cup and venting means according to this invention.

Referring to FIG. 1, there is shown a top view of a sample cup 10 employing venting means according to this invention.

Figure 2:
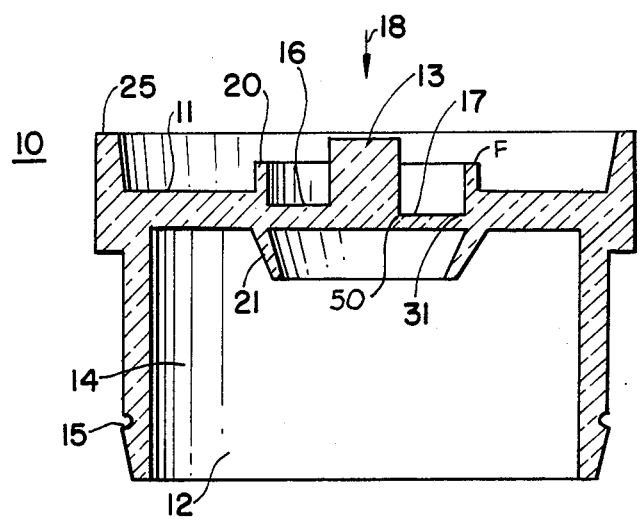
FIG. 2 is a cross sectional view taken through line 2—2 of FIG. 1.

FIG. 2 shows a cross sectional view taken through line 2—2 of FIG. 1.

As one can see, the sample cup 10 has a closed bottom surface 11 with an open top surface 12. The sample is typically in place within the hollow 14 of the cup after the cup is turned upside down, and the open top is then covered by means of a MYLAR sheet which sheet is retained by an annular ring which has a coacting flange which is positioned by means of the peripheral notch 15 in the wall of the sample cup.

Essentially, the annular ring as well as the plastic film are not shown as they are not pertinent to the aspects of this invention. The entire sample cup arrangement is clearly depicted in U.S. Pat. No. 4,409,854 as referenced above.

As one can see from FIG. 1, centrally located on the closed surface 11 of the cup is an upstanding post 13 which post is integrally formed with a cantilever beam section 16. The beam section 16 is surrounded by a thin wall section 17 which as will be explained ruptures or breaks creating a venting means when the post 13 is pushed downwardly or in the direction of arrow 18 of FIG. 2.

Surrounding the cantilever beam and post is a concentric circular upstanding flange section 20. This circular flange section acts as a thumb stop or a thumb rest to allow a user to push open the post with his thumbnail using the upstanding circular flange as a support where the flange further acts as an intermediate reservoir for any sample which may escape from the internal hollow 14 of the cup during the venting process.

As seen from FIG. 2, the cantilever section 16 which is a rectangular section emanates from the circular flange 20 and is terminated in an upstanding post 13. Surrounding the cantilever member 16 is a thin wall section 17. Located beneath the circular flange 20 is an internal flange or rim member 21. The rim member 21 forms a receptacle for the internal hollow 14 of the cup, and that receptacle can be utilized to hold a rod or other such device which can be useful in performing spectrochemical analysis on certain specimens.

For an example of such a rod in greater detail, reference is made to U.S. Pat. No. Des. 2,386,693 entitled Cell for X-ray Spectroscopy or Similar Article issued Feb. 3, 1976 to Monte J. Solazzi. The entire cup may be integrally molded and is typically fabricated from a suitable plastic such as polypropylene. Such plastic as polyproplylene and other plastics as well offer rigidity while exhibiting a greater resistance to chemical attack.

Also shown in FIGS. 1 and 2 is an outer upstanding peripheral flange 25. Flange 25 as well as flange 20 both serve or act as a reservoir to capture or contain any fluid or material which may escape from the sample cup when providing venting. Hence any escaped material will be prevented from spilling due to the peripheral flange 25 as well as the internal concentric flange 20 both of which operate to serve as reservoirs.

Essentially, operation of the venting means is as follows. The cantilever beam 16 appears as a spring broad with the post 13 coupled thereto. Hence if one pushes the post downwardly, the cantilever will move downward causing a detachment at either points 30 or 31. This is due to the stress imposed upon the post and the consequent movement of the cantilever beam. Thus as one can ascertain, there is a break in the thin wall section 17 which break may occur at points 30 or 31. The cantilever beam springs back into position after it has provided venting to allow pressure equalization.

Thus in this invention the cantilever beam 16 acts as a spring board, and hence one breaks the thin section 17 while the spring board action of the beam 16 returns the beam to its original position thus preventing a large seepage of material while establishing pressure equalization.

In regard to the above noted configuration, by pushing the post 13 downwardly, one will rupture the thin wall area 17 but the cantilever beam will spring back after equalization and hence assume the position shown in FIG. 2 with a tendency to reclose the vent. This action provides for a minimum seepage of material during the venting process.

Smaller quantities of material will be contained within the flange 20 while larger volumes of escaped material may spill over into the reservoir portion formed by the peripheral flange 25. While it is shown that the width of the cantilever beam is thicker than section 17, it is noted that the width of the cantilever beam may be as wide as the width of the closed bottom surface.

The above noted structure provides a rapid venting means enabling an operator to utilize a finger to push down upon the post which will therefore rupture the thin surrounding area with the cantilever giving a large force advantage while acting as a spring to attempt to return the post to its initial quiescent condition thus preventing undue escape of liquid samples.

I claim:

1. A sample cup body for retaining a specimen to be subjected to spectrochemical analysis, said sample cup body comprising a closed bottom surface and an open top, said closed bottom surface comprising integral venting means having a predetermined periphery defining a venting area of said closed bottom surface and including upstanding post means centrally located within said predetermined periphery, a cantilever beam section extending from a predetermined location on said periphery of said venting means to said upstanding post means and comprising a first portion of said venting area, said cantilever beam section having a first thickness, and said upstanding post means being positioned on said cantilever beam section, and a thin walled section extending from said periphery of said venting means to said upstanding post means and comprising a second portion of said venting area, said thin walled section having a second thickness, said second thickness being substantially less than said first thickness and said second portion of said venting area being substantially greater than said first portion of said venting area, whereby when said upstanding post means is pushed downwardly said thin walled section is caused to rupture thereby providing venting through said venting means.

2. The sample cup body of claim 1 wherein said predetermined periphery is circular, and said upstanding post means is located at the center of said circular periphery.

3. The sample cup body of claim 2 including an upstanding circular flange located around said circular periphery and surrounding said upstanding post means.

4. The sample cup body of claim 3 including upstanding inner circular flange means on the opposite surface of said closed bottom from said upstanding circular flange means at a location corresponding thereto.

5. The sample cup body of claim 2 wherein said cantilever beam section is substantially rectangular in configuration, and wherein said thin walled section is substantially annular surrounding said upstanding post means except for said cantilever beam section.

6. The sample cup body of claim 1 including an upstanding outer peripheral flange surrounding said closed bottom surface.

7. The sample cup body of claim 1 wherein said entire sample cup body is integrally formed from a chemically resistant plastic.

8. The sample cup body of claim 7 wherein said plastic comprises polypropylene.

* * * * *